United States Patent [19]

Patterson

[11] Patent Number: 5,129,940
[45] Date of Patent: Jul. 14, 1992

[54] POLLEN SUPPRESSANT FOR LILIOPSIDA PLANTS COMPRISING A 5-OXY-SUBSTITUTED CINNOLINE

[75] Inventor: Thomas G. Patterson, Pleasanton, Calif.

[73] Assignee: Orsan, Paris, France

[21] Appl. No.: 748,412

[22] Filed: Aug. 22, 1991

[51] Int. Cl.$^5$ ............................................. A01N 43/58
[52] U.S. Cl. ........................................... 71/92; 71/114
[58] Field of Search ................................ 71/92

[56] References Cited

U.S. PATENT DOCUMENTS

| 4,560,401 | 12/1985 | Devlin | 71/88 |
| 4,915,727 | 4/1990 | Mizutani et al. | 71/92 |
| 4,925,477 | 5/1990 | McDaniel | 71/92 |

FOREIGN PATENT DOCUMENTS 0363236  4/1990  European Pat. Off. .

Primary Examiner—Carolyn Elmore
Assistant Examiner—S. Mark Clardy
Attorney, Agent, or Firm—Cooley, Godward, Castro, Huddleson & Tatum

[57] ABSTRACT

Pollen is suppressed in Liliopsida by use of compounds of the formula

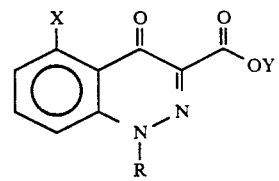

wherein X represents a group of the formula OR$^1$ wherein R$^1$ represents a C$_1$–C$_4$ alkyl optionally substituted with a C$_1$–C$_4$ alkoxy group; or C$_2$–C$_4$ and R represents phenyl or phenyl substituted with one to three halogen atoms or C$_1$–4 haloalkoxy; or an agriculturally acceptable salt thereof are disclosed along with methods to produce hybrid seed in self-fertilizing plants.

12 Claims, No Drawings

POLLEN SUPPRESSANT FOR LILIOPSIDA PLANTS COMPRISING A 5-OXY-SUBSTITUTED CINNOLINE

INTRODUCTION

1. Technical Field

The present invention relates to a method of regulating the fertility of Liliopsida plants using 5-oxy-substituted cinnoline compounds.

2. Background

It is possible to inhibit self-pollination in wheat and similar plants by chemically inhibiting the formation of pollen or by inducing the plant to produce non-functioning pollen. Several compounds have previously been developed which produce these effects.

U.S. Pat. No. 4,345,934 discloses a compound of the formula:

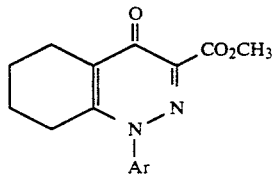

where Ar is 4'-chlorophenyl and an attempt to use this compound as a pollen suppressant. However, this compound was not active as a gametocide.

Zh. Obshch. Khim. (1967) 37:2487, as abstracted in Chem. Abstracts, (1968) 69:36059, discloses a compound of the formula:

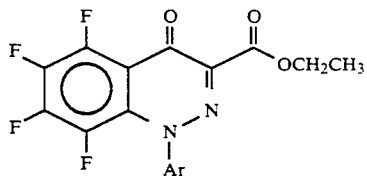

where Ar is phenyl substituted with halogen. However, this publication is directed only to synthesis and no use for the compound is disclosed.

U.S. Pat. Nos. 4,604,134 and 4,729,782 disclose cinnolines with various substituents and the use of these compounds as chemical pollen suppressants. Some 5-alkoxycinnolines are encompassed by the generic formulas set forth in the patents, but such compounds are not emphasized, the preferred compounds being 5-fluorocinnolines. A 6-dimethylaminocinnoline derivative is listed as a typical compound, but no 5-alkoxycinnolines or derivatives thereof are specifically listed.

U.S. Pat. No. 4,915,727 discloses cinnolines with various 5-substitutions and a 1-(haloalkoxyphenyl)-substitution as male sterilants, particularly for wheat, rice and morning glory.

European patent no. 320,782 discloses cinnolines with a 5-haloalkoxy substitution and certain 1-(substituted-phenyl)-substitutions as male sterilants, particularly for wheat, rice and morning glory.

Nevertheless, many of the compounds so far tested have adverse effects on hybrid seed quality or injure plants at doses only slightly above those required to produce maximum male plant sterility. Properties of prospective gametocides can vary with the chemical used and on the type of plant to be induced to male sterility. Accordingly, a continued need for new pollen suppressants useful for producing hybrid seed exists.

SUMMARY OF THE INVENTION

It is an object of this invention to provide a method of suppressing pollen production in Liliopsida plants using certain cinnoline compounds.

It is a further object of this invention to provide a method for producing hybrid seed of Liliopsida plants using the chemical sterilants of the invention.

These and other objects of the invention as will hereinafter become more readily apparent have been accomplished by providing a chemical pollen suppressant of the formula:

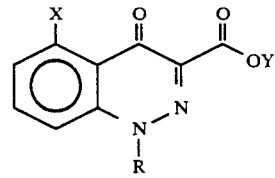

wherein X represents a group of the formula $OR^1$ wherein $R^1$ represents a $C_1$-$C_4$ alkyl optionally substituted with a $C_1$-$C_4$ alkoxy group or a $C_2$-$C_4$ alkenyl group;

Y is hydrogen or $C_1$-$C_6$ alkyl; and

R represents phenyl or phenyl substituted with one to three halogen atoms or $C_{1-4}$ haloalkoxy;

or an agronomically acceptable salt thereof.

DESCRIPTION OF THE PREFERRED EMBODIMENTS

The present invention provides certain cinnolines in which an alkoxy substituent is present at position 5 of the cinnoline ring and a phenyl substituent is present at position 1 of the cinnoline ring. Thus, the chemical pollen suppressants of the invention include those compounds having the formula:

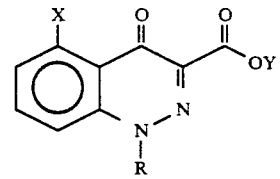

wherein X represents a group of the formula $OR^1$ wherein $R^1$ represents a $C_1$-$C_4$ alkyl optionally substituted with a $C_1$-$C_4$ alkoxy group or a $C_2$-$C_4$ alkenyl group;

Y is hydrogen or $C_1$-$C_6$ alkyl; and

R represents phenyl or phenyl substituted with one to three halogen atoms or $C_{1-4}$ haloalkoxy;

or an agronomically acceptable salt thereof.

Such compounds provide balanced male sterility activity and phytotoxicity when applied to Liliopsida and can be applied during different stages of growth over a wider range of dosages compared to the most closely related compounds that were previously known.

The compounds of the invention provide a better balance of overall properties including the ability to induce male sterility over a relatively large dose range, good seed set, and low phytotoxicity.

In one preferred embodiment of the invention, —CO₂Y is a carboxy group or a salt thereof. When —CO₂Y is a salt of a carboxy group, the cation can be an alkali metal ion, alkaline earth metal ion, or transition metal ion. The cation can also be an ammonium or substituted ammonium ion. Representative alkali metal ions, which are preferred, include lithium, sodium and potassium ions; representative alkaline earth metal ions include magnesium, calcium, and barium ions; representative transition metal ions include zinc, manganese, iron, titanium, and molybdenum ions; and representative ammonium ions, which are also preferred, include the ammonium ion itself and alkyl-substituted ammonium ions (especially alkanol-substituted ammonium ions).

The phenyl group R is preferably unsubstituted phenyl or phenyl 4'-substituted with one halogen atom, preferably with chlorine or fluorine; Y is H, Na or K; and X represents a group of the formula OR¹ wherein R¹ represents a C₁-C₄ alkyl optionally substituted with a C₁-C₄ alkoxy group.

Preferred esters include those prepared from linear and branched C₁-C₆ alkanols.

At the Y location, tetrabutyl ammonium and tetramethyl ammonium salts are especially preferred along with ammonium salts containing alkanol substituents in place of alkyl substituents. Preferred —CO₂Y groups are acids and acid salts, although esters as described above are nearly as preferred. Among acid salts, quaternary ammonium salts are preferred, as they enhance solubility. X is preferably a —OMe, —OEt, —OnPr, —OiPr, —OiBu, —OCH₂CH₂OCH₃, or —OCH₂CH₂OCH₂CH₃.

Preferred compounds are defined by selecting one or more of these listings of preferred substituents in combination with the general formula previously given. Certain combinations of substituents are especially preferred. One preferred grouping occurs when R is phenyl 4'-substituted with a chlorine or fluorine atom Y is —H, —Na, or K; and X represents —OMe, —OEt, —OnPr, —OiPr, —OiBu, —OCH₂CH₂OCH₃, or —OCH₂CH₂OCH₂CH₃.

Preferred compounds are defined by selecting one or more of these listings of preferred substituents in combination with the general formula previously given. Certain combinations of substituents are especially preferred. One preferred grouping occurs when R is phenyl 4'-substituted with a chlorine or fluorine atom Y is —H, —Na, or K; and X represents —OMe, —OEt, —OCH₂CH₂OCH₃ or —OCH₂CH₂OCH₂CH₃.

Also included within the scope of the invention are agronomically acceptable acid addition salts of compounds having the general formula given. Typical acid addition salts are those formed with strong acids such as hydrochloric, hydrobromic, and sulfuric acids. Salts of acidic or basic functional groups, such as the —CO₂Y or —X groups, are also included in this invention. Throughout this application, agronomically acceptable salt means that the salt is not substantially more toxic to the plant or to the consumer of the plant than the parent compound from which the salt is formed.

Typical compounds of the invention include the following:

1-(4'-chlorophenyl)-1,4-dihydro-4-oxo-5-ethoxycinnoline-3-carboxylic acid 1-(4'-fluorophenyl)-1,4-dihydro-4-oxo-5-ethoxycinnoline-3-carboxylic acid 1-(4'-chlorophenyl)-1,4-dihydro-4-oxo-5-n-propyloxycinnoline-3-carboxylic acid 1-(4'-chlorophenyl)-1,4-dihydro-4-oxo-5-methoxycinnoline-3-carboxylic acid 1-(4'-fluorophenyl)-1,4-dihydro-4-oxo-5-i-butoxycinnoline-3-carboxylic acid 1-(4'-trifluoromethoxyphenyl)-1,4-dihydro-4-oxo-5-methoxycinnoline-3-carboxylic acid as well as the ammonium, sodium, potassium, and lithium carboxylate salts of each of the above compounds and the acid addition salts of each of the above listed compounds. By carboxylate salt is meant a salt of a carboxylic acid group at C-3. By acid addition salt is meant a salt formed by the protonation of a ring or side chain nitrogen.

The compounds of the invention can be synthesized according to known methods for the production of analogous compounds or can be produced by synthetic modification of known pyridazines or cinnolines. For example, numerous synthetic pathways to cinnolines are described in *Condensed Pyridazines Including Cinnolines and Phthalazines*, R. N. Castle, ed., John Wiley and Sons, N.Y., 1973, pages 1–321 of which are herein incorporated by reference. For example, one suitable method involves the reaction of readily accessible diethyl mesoxalate diphenylhydrazones of the formula:

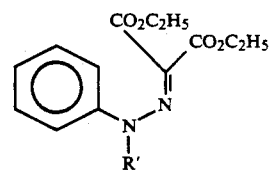

in which R' represents a substituted phenyl group previously named, with an ethanolic base to give a dicarboxylic acid. This acid is converted into a diacid chloride using a suitable reagent, such as thionyl chloride. The acid chloride then undergoes a Friedel-Crafts acylation reaction, for example in nitrobenzene at about 100° C. in the presence of TiCl₄. A product having the following formula is obtained:

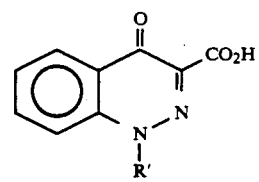

wherein R' has the previously given meanings. Although this reaction is shown with an unsubstituted phenyl group for the sake of simplicity, other aromatic rings or substituents such as substituents in the 4'-position, may also be present, although at least one ortho position of the diphenylhydrazone must be free in order that the Friedel-Crafts reaction can take place. Groups that would interfere with this ring-forming reaction may be present in protected form (e.g., an acylamino group that may later be converted into an amine) or they may be added later (e.g., by halogenation of the phenyl rings) or they may be prepared by conversion of a suitable group present during synthesis.

Another general synthetic method for synthesizing compounds of the invention is described in *Synthesis*, pages 52–53 (1983), which is also herein incorporated by reference. In this reaction sequence, the key step is condensation of an intermediate of the formula:

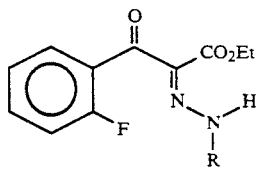

where R has the meanings previously defined and F may optionally be a nitro group rather than fluorine. This reaction is also shown for simplicity as forming an unsubstituted cinnoline.

The above-indicated 3-carboxycinnolines can then be converted into other compounds of the invention by known methods. For example, the carboxylic acid group can be converted into a carboxylate salt or a protected amino group can be deprotected, diazotized, and converted into a different functional group.

Various modifications of these reactions and of other reactions capable of modifying the initially formed cyclic compounds can be used to produce all the compounds of the present invention, for example, as is disclosed in four of the prior art patents previously cited (U.S. Pat. No. 4,345,934, U.S. Pat. No. 4,115,727, DOS 28 08 795, EP 37 133, EP 320 782, and EP 49 971), which are herein incorporated by reference.

A series of compounds has been synthesized using techniques such as the methods described above, and some of these compounds have been tested for ability to induce male sterility using the procedure set forth in Example 2 which follows. Representative compounds are shown in Table 1 below. Some of those compounds are used in male sterility induction experiments as salts.

EXAMPLE 1

Synthesis of 1-(4'-chlorophenyl)-1,4-dihydro-4-oxo-5-fluorocinnoline-3-carboxylic acid Using the general procedure of Wierenga and Skulnick (J. Org. Chem. (1979) 44:310), a solution of 3.0 g (22.6 mmole) of monoethyl malonate in 40 ml of dry THF containing 2 mg of 2,2'-dipyridyl was treated at $-75°$ C. with 29.2 ml of 1.5 M butyllithium (45.28 mmole) in hexane in such a way that the temperature was maintained below $-60°$ C. The temperature was allowed to reach $-5°$ C. and lowered again to $-70°$ C. at which time 11.32 mmole of 2,6-difluorobenzoyl chloride in 15 ml of dry THF was added while the temperature was maintained at or below $-60°$ C. The mixture was allowed to reach room temperature over 2 hours with continual stirring. After dilution with ether and treatment with 40 ml of 1N HCl the mixture was worked up in the normal fashion to provide after distillation of the organic residue, 6.9 g (67%) of product b.p. 117°–119° C./1 Torr.

A solution of the benzoylacetate (38.8 g, 0.17 mole) in aqueous methanol containing 0.51 mole of potassium acetate was treated with an aqueous solution of p-chlorophenyldiazonium chloride (derived from 0.18 mole p-chloroaniline) at 10°–15° C. The resulting precipitate was recrystallized from aqueous methanol, dried in vacuo overnight and then dissolved in 300 ml of dry DMF. To this solution was added 11.0 g of anhydrous potassium carbonate and 50 mg of 18-crown-6. The mixture was heated with stirring to 100° C. for 1 hour. The reaction mixture was cooled and diluted with water, and the precipitate was collected and dried to yield 39 g of the desired cinnoline carboxylate ethyl ester m.p. 158°–160° C. The acid desired was obtained by saponification in ethanol at room temperature containing one equivalent of potassium hydroxide, reacidification and filtration of the resulting precipitate, m.p. 246°–247° C.

EXAMPLE 1A

General Procedure for the Synthesis of 5-alkoxycinnolines From 5-halo Precursors To one equivalent of the 5-halo precursor, which can be prepared according to the procedure set forth in Example 1, in a solution of dioxane is added a solution of the desired potassium alkoxide in paradioxane. The mixture is stirred in an inert atmosphere at room temperature with mild heating used in more sluggish cases. The course of the reaction is monitored by high-pressure liquid chromatography (HPLC). When the reaction is complete, the pH is adjusted to pH 4, the mixture is diluted with water, and the precipitated product is filtered to yield the desired 5-alkoxy derivative (yields normally are in excess of 90%).

TABLE 1

Synthesized Compounds of the Invention

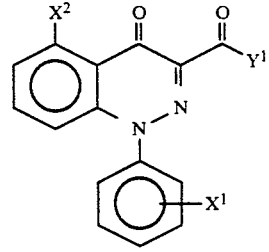

| Compound | $X^1$ | $X^2$ | $Y^1$ |
|---|---|---|---|
| 1 | 4'-Cl | $OCH_3$ | $OCH_3$ |
| 2 | 4'-Cl | $OCH_3$ | OH |
| 3 | 4'-Cl | $OCH_2CH_3$ | OH |
| 4 | 4'-Cl | OiPr | OH |
| 5 | 4'-F | $OCH_3$ | OH |
| 6 | 4'-F | $OCH_2CH_3$ | OH |
| 7 | 4'-F | OiPr | OH |
| 8 | 4'-Cl | $O-n-C_4H_9$ | OH |
| 9 | 4'-F | $O-n-C_4H_9$ | OH |
| 10 | 4'-Cl | $OCH_2CH_2OCH_3$ | OH |
| 11 | 4'-F | $OCH_2CH_2OCH_3$ | OH |
| 12 | 4'-Cl | $OCH_2CH(CH_3)_2$ | OH |
| 13 | 4'-F | $OCH_2CH(CH_3)_2$ | OH |
| 14 | 4'-Cl | $OCH_2CH_2OCH_2CH_3$ | OH |
| 15 | — | $OCH_3$ | OH |
| 16 | 2'-F | $OCH_3$ | $OCH_3$ |
| 17 | 2'-F | $OCH_3$ | OH |
| 18 | 2',3'-diF | $OCH_3$ | OH |
| 19 | 3',4'-diF | $OCH_3$ | OH |
| 20 | 2'-F,4'-Cl | $OCH_3$ | OH |
| 21 | 2'-Cl | $OCH_3$ | OH |
| 22 | 2',4'-diCl | $OCH_3$ | OH |
| 23 | 4'-$OCF_3$ | $OCH_3$ | OH |
| 24 | 2'-F,4'-Cl | $OCH_3$ | OH |
| 25 | 2',4'-diF | $OCH_3$ | OH |
| 26 | 2',4',6'-triF | $OCH_3$ | OH |
| 27 | 3'-F,4'-Cl | $OCH_3$ | OH |
| 28 | 3'4'-diCl | $OCH_3$ | OH |
| 29 | 3'-F | $OCH_3$ | OH |
| 30 | 2',5'-diF | $OCH_3$ | OH |
| 31 | 3',4'-diF | $OCH_2CH_3$ | OH |
| 32 | 3',4'-diF | $OCH(CH_3)_2$ | OH |
| 33 | 2',3'-diF | $OCH_2CH_3$ | OH |
| 34 | 2',3'-diF | $OCH(CH_3)_2$ | OH |
| 35 | 2',6'-diF | $OCH_3$ | OH |
| 36 | 2',6'-diF | $OCH_2CH_3$ | OH |

TABLE 1-continued
Synthesized Compounds of the Invention

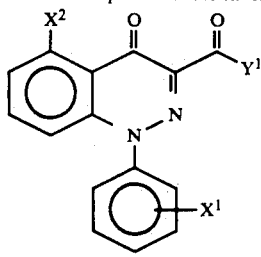

| Compound | X¹ | X² | Y¹ |
| --- | --- | --- | --- |
| 37 | 2',6'-diF | OCH(CH$_3$)$_2$ | OH |
| 38 | 2'-F, 4'-Cl | OCH$_2$CH$_3$ | OH |
| 39 | 2'-Cl,4'-F | OCH(CH$_3$)$_2$ | OH |
| 40 | 3'-Cl,4'-F | OCH$_2$CH$_3$ | OH |
| 41 | 3'-Cl,4'-F | OCH$_3$ | OH |
| 42 | 2'-Cl,4'-F | OCH$_2$CH$_3$ | OH |
| 43 | 2'-Cl,4'-F | OCH(CH$_3$)$_2$ | OH |
| 44 | 3'-Cl,4'-F | OCH(CH$_3$)$_2$ | OH |
| 45 | 2',4'-diF | OCH(CH$_3$)$_2$ | OH |
| 46 | 2',4'-diF | OCH$_2$CH$_3$ | OH |
| 47 | 4'-OCF$_3$ | OCH(CH$_3$)$_2$ | OH |
| 48 | 4'-OCF$_3$ | OCH$_2$CH$_2$CH$_2$CH$_3$ | OH |
| 49 | 3'-F,4'-Cl | OCH$_2$CH$_2$CH$_3$ | OH |
| 50 | 4'-OCF$_3$ | OCH$_2$CH$_2$CH$_3$ | OH |
| 51 | 4'-OCF$_3$ | OCH$_2$CH(CH$_3$)$_2$ | OH |
| 52 | 2'4'-diF | OCH$_2$CH$_2$CH$_3$ | OH |
| 53 | 2'-F | OCH$_2$CH$_2$CH$_3$ | OH |
| 54 | — | OCH$_2$CH$_2$CH$_3$ | OH |
| 55 | — | OCH$_2$CH=CH$_2$ | OH |

Compounds of the invention are useful as chemical hybridization agents in Liliopsida plants, including plants of the subclass Liliidae, plants of the order Liliales, plants of the family Liliaceae, plants of the genus Allium, and especially onion plants, *A. cepa*. Of these, treatment of onion crops is preferred. Different effects will be obtained depending upon the growth stage of the plant when treated. Compounds of the invention induce selected male sterility without also inducing unacceptable female sterility. About 30% female fertility is generally acceptable, although this level may differ when the method is used commercially, based on the economics of $F_1$ seed production. As used herein, the term male sterility includes sterility caused by lack of male flower parts, by formation of sterile pollen, and by male flower parts which produce normal pollen but are functionally unable to cause pollination.

When compounds of the invention are used in hybridization, they are used in an amount sufficient to produce the effect of male sterility without producing an unacceptable phytotoxic reaction or other undesired side-reaction. Compounds of the invention are generally applied at a rate of from 0.025 to 20.0 pounds per acre, and preferably from 0.125 to 10.0 pounds per acre. The amount used depends upon the plant type and the method of application as is well-known to those skilled in the art and can be determined by simple experimentation if not known.

Although any method of hybridization may be used, the following method generally is sufficient. The two parent strains to be crossed are planted in alternate sections, rows, or groups of rows. The female parent is treated with a compound of the invention in order to render this parent male sterile. Pollen from the male (untreated) parent then fertilizes the female parent, either by means of human intervention or preferably by means of a natural process, such as windborne or insect pollination. The seed produced by the female parent is an F-1 hybrid, which is then collected according to conventional techniques.

Compounds of the invention are very effective for inducing male sterility in Liliopsida when they are applied to the medium in which plants are grown such as soil surface in an onion field. Another method of applying the compounds of the invention for otherwise inducing male sterility is foliar application directly to the flowering stalk. When this method is used, very selective male sterility can be obtained when the compound is applied between the beginning of bloom and the beginning of meiosis. Compounds of the invention can also be applied directly to seed in order to cause male sterility, whereby the seeds are dipped into a fluid formulation containing the active ingredient. Seed can also be sprayed with a solution or suspension containing a compound of the invention. In general, seed are treated with a compound of the invention in an amount of from about ¼ to 10 pounds per 100 pounds of seed.

Compounds of the invention can be used as hybridization materials together with other plant regulatory agents, for example, in mixtures with these compounds. Examples of plant regulating materials which can be used include auxins, gibberellins, ethylene liberating materials such ag Ethephon, pyridones, cytokinins, maleic hydrazide, carbonic acid, 2,2-dimethyl hydrazide, cholines (as well as their salts), (2-chloroethyl)-trimethylammonium chloride, triiodobenzoic acid, tributyl-2,4-dichlorobenzenephosphonium chloride, polymeric N-vinyl-2-oxazolidinones, tri(dimethylaminoethyl)phosphate, and salts of these compounds as well as N-dimethylamino 1,2,3,6-tetrahydrophthalamides and their salts. Compositions containing one or more compounds of the invention in a 1:99-99:1 ratio to one or more different compounds having plant regulatory activities may be prepared. Likewise, compounds of the invention may be prepared into compositions useful for other agricultural purposes, such as herbicides, fungicides, insecticides, and plant bactericides.

A compound of the invention can be applied to a plant either as itself or in combination with other plant growth regulators. A composition containing a compound of the invention and any other active ingredient can be diluted with an agronomically suitable carrier, which is any substance which itself is without any significant effect on plants but which is added in order to allow simpler application of the active ingredients to plants. Carriers include both liquids and solids. Accordingly, compositions of the invention can be either solid or liquid formulations or solutions. For example, the compounds can be used in powders, emulsifiable concentrates, dusts, pellets, aerosols and solutions. In any of the various formulations, a surface active agent may be added in order to increase uptake of the active compounds. It is especially preferred, and particular for methods which involve application to leaves, to utilize agents which aid in the application of the material, for example, dispersion agents and detergents.

Compounds of the invention can be dissolved in any suitable solvent. Examples of solvents which can be used include water, alcohols, ketones, aromatic hydrocarbons, halogenated hydrocarbons, dimethylformamide, dioxane, and dimethylsulfoxide. Mixtures of these solvents can likewise be used. The concentration of these solutions can be from about 2 to about 98% by weight of active ingredient and is preferred to be in the range from about 20 to about 75% by weight.

In order to produce emulsifiable concentrates, the compounds of the invention are dissolved in an organic solvent, such as benzene, toluene, xylene, methylated naphthalene, corn oil, turpentine, o-dichlorobenzene, isophorone, cyclohexane, or methyl oleate or in mixtures of these solvents, together with an emulsifying material which allows the dispersion in water. Suitable emulsifying agents include ethylene oxide derivatives of alkylphenols or long-chained alcohols, mercaptans, carboxylic acids, and reactive amines, and especially high molecular weight alcohols. Solvent-soluble sulfates or sulfonates, such as the alkaline earth salts or amine salts of alkylbenzene-sulfonates as well as sodium fatty alcohol sulfates with surface active properties can be utilized as emulsifying agents either alone or in combination with an ethylene oxide reaction product. Free-flowing emulsion concentrates are formulated similarly to emulsifiable concentrates and contain, in addition to the previously described components, water as well as a stabilizing agent, such as a water-soluble cellulose derivative or a water-soluble salt of a polyacrylic acid. The concentration of the active ingredient in the emulsifiable concentrate is generally about 10 to 60 wt. % and in free-flowing emulsion concentrates is generally about 10 to 60% or sometimes up to 75% by weight.

When a powder containing the compound of the invention is being prepared, the active ingredient is usually mixed with a finely divided solid, such as a clay, an organic silicate or carbonate, or a silica gel along with an agent capable of holding together the resulting materials. The concentration of the active ingredient in such powders generally lies between about 20 and 98% by weight and preferably lies between 40 and 75% by weight. A dispersion material can generally be present in an amount of about 0.5 to 3% by eight of the entire powder. An agent may be added in order to control water absorption and if added is generally present in an amount of about 0.1 to about 5% by weight of the total powder.

Dusts can be prepared by mixing the active ingredient with a finely divided inert solid, which can be of an organic or inorganic nature. Suitable material for this purpose include flour, farina, diatomite, silicates, carbonates, and clays. A satisfactory method for the production of dusts involves crushing a wettable powder together with a finely divided carrier. A dust concentrate, which contains from about 20 to about 80% of the active ingredient, is produced according to known methods and then diluted to form a final concentration of the compound of the invention of about 1 to about 10% by weight of the dust.

Particulate formulations can be prepared by any known method, for example by impregnating the active ingredient into a solid material, such as particulate Fullers earth, vermiculite, cornmeal, seed hulls guch as grain hulls, or other materials. A solution of one or more of the compounds of the invention in a freely flowing organic solvent can be applied to the particulate solid or mixed therewith, after which the solvent is evaporated away. The particulate material is not limited to a particular size. However, a useful size is from 16 to 60 mesh (U.S. standard mesh size). The active ingredient generally occupied about 2 to about 15 wt. of the particulate formulation.

Salts of the compounds of the invention can be prepared as aqueous solutions and applied in this form. The salts occupy typically about 0.05 to about 50 wt. % and preferably from about 0.1 to 10 wt. % of the solution. In any event, these solutions may be diluted with additional water prior to use. In some cases the activity of the active material can be increased by including another agent in the solution, such as glycerin, methylethylcellulose, hydroxyethyl cellulose, polyoxyethylene sorbitol mono-oleate, polypropylene glycol, polyacrylic acid, polyethylene sodium malonate, or polyethyleneoxide. The auxiliary occupies generally from about 0.1 to about 5 wt. % and particularly from about 0.5 to 2 wt. % of the solution. The various solutions can in any case also contain an agriculturally suitable surface active agent.

The compounds of the invention can be applied to Liliopsida according to any known methods, for example in the form of hydraulic sprays, air sprays or dusts. For methods which involve the application of small volumes, a solution of the compound is generally utilized. The volume used and the rate of application depend upon various factors which vary with the method used, such as the specific type of application method, the stage of development of the plant to which the active ingredient is being applied, and other factors well known to those skilled in the art or easily determined by simple experimentation.

Having now generally described this invention, the same will be better understood by reference to the following example which is included herein for purposes of illustration only and is not intended to be limiting of the invention or any embodiment thereof, unless so specified.

EXAMPLE 2

Onions

Field trial with onions were conducted with short day onions in San Juan Bautista, Calif. and with long day onions in Nampa, Id. Compounds 5 and 10 of the invention were each tested at 4 or 5 dosages. The compounds were applied foliarly with hand held spray bottles. Each compound was formulated as a water soluble solution with 0.4% Triton AG-98 v/v as a low foam surfactant. The results of these tests are set forth in Tables 2 and 3 below. These results demonstrate that Compound 10 of the invention was less toxic to the onions than Compound 5 at the dosages used in the tests. Good male sterility (based on visual ratings) was induced at all dosages of Compound 10. The higher dosages caused some phytotoxicity to the flower. Compound 5 was more phytotoxic than Compound 10 and there was less separation between male sterility and phytotoxicity. Open pollinated seed set was reduced in the treated plants to some degree.

TABLE 2

| Short Day Onions | | |
| --- | --- | --- |
| Compound | g/l | % Male Sterility |
| 10 | 0.9 | 90–95 |
| 10 | 1.7 | 100 |
| 10 | 2.6 | 100 |
| 10 | 3.4 | 100 |
| 5 | 1.4 | 100 |
| 5 | 2.9 | 100 |
| 5 | 4.3 | 100 |
| 5 | 5.7 | 100 |

TABLE 3

| | Long Day Onions | |
|---|---|---|
| Compound | g/l | % Male Sterility |
| 10 | 0.9 | 100 |
| 10 | 1.4 | 100 |
| 10 | 2.0 | 100 |
| 10 | 2.6 | 100 |
| 10 | 3.1 | 100 |
| 10 | 3.7 | 100 |
| 5 | 0.9 | 100 |
| 5 | 1.4 | 100 |
| 5 | 2.0 | 100 |
| 5 | 2.6 | 100 |
| 5 | 3.1 | 100 |
| 5 | 3.7 | 100 |

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of inducing male sterility in a Liliopsida plant, which comprises treating said plant, a seed from which said plant is to be grown or a medium in which said plant is growing or is to be grown with an effective amount of a pollen suppressant of the formula

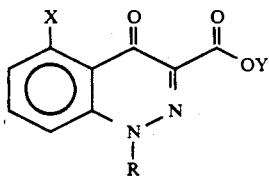

wherein:
X represents a group of the formula $OR^1$ wherein $R^1$ represents a $C_1$-$C_4$ alkyl group optionally substituted with a $C_1$-$C_4$ alkoxy group or $C_2$-$C_4$ alkenyl;
Y is hydrogen or $C_1$-$C_6$ alkyl; and
R represents phenyl or phenyl substituted with one to three halogen atoms or $C_{1-4}$ haloalkyoxy;
or an agronomically acceptable salt thereof.

2. The method of claim 1, wherein Y is —H or a salt thereof.

3. The method of claim 1, wherein X is $C_1$-$C_2$ alkoxy or $C_1$-$C_2$ alkoxy substituted with $C_1$-$C_2$ alkoxy.

4. The method of claim 1, wherein R is phenyl or phenyl 4'-substituted with a substituent $X^1$ selected from the group consisting of 4'-chloro and 4'-fluoro.

5. The method of claim 4, wherein R is phenyl substituted with $X^1$ wherein $X^1$ is 4'-F, X is —$OCH_3$, and Y is —H or a salt thereof.

6. The method of claim 4, wherein R is phenyl substituted with $X^1$ wherein $X^1$ is 4'-Cl, X is —$OCH_2CH_2OCH_3$, and Y is —H or a salt thereof.

7. The method of claim 1 wherein the plant is an Allium plant.

8. The method of claim 7 wherein the plant is onion.

9. The method of claim 1 wherein the plant is treated by applying the pollen suppressant as an aqueous solution thereof to the medium in which said plant is growing.

10. A method of producing hybrid seeds from a self-pollenizing Liliopsida plant which comprises sterilizing the male anthers of a female parent plant with a pollen suppressant and pollinating said female parent with pollen from an untreated male parent, thereby producing said hybrid seed; wherein said pollen suppressant is a compound of the formula

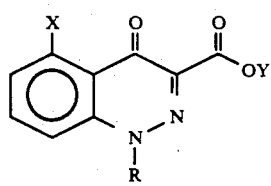

wherein:
X represents a group of the formula $OR^1$ wherein $R^1$ represents a $C_1$-$C_4$ alkyl group optionally substituted with a $C_1$-$C_4$ alkoxy group or $C_2$-$C_4$ alkenyl;
Y is hydrogen or $C_1$-$C_6$ alkyl; and
R represents phenyl or phenyl substituted with one to three halogen atoms or $C_{1-4}$ haloalkoxy;
or an agronomically acceptable salt thereof.

11. The method of claim 10, wherein said hybrid seed is seed from an Allium plant.

12. The method of claim 11, wherein said seed is onion seed.